US00PP27220P3

(12) United States Plant Patent
Bédard

(10) Patent No.: US PP27,220 P3
(45) Date of Patent: Oct. 4, 2016

(54) CLIMBING MINIATURE ROSE PLANT NAMED 'WEKWOAGOROL'

(50) Latin Name: *Rosa hybrida*
Varietal Denomination: WEKwoagorol

(71) Applicant: Early Morning LLC, Pomona, CA (US)

(72) Inventor: Christian Bédard, Placentia, CA (US)

(73) Assignee: EARLY MORNING LLC, Pomona, CA (US)

( * ) Notice: Subject to any disclaimer, the term of this patent is extended or adjusted under 35 U.S.C. 154(b) by 110 days.

(21) Appl. No.: 14/544,065

(22) Filed: Nov. 20, 2014

(65) Prior Publication Data
US 2016/0150690 P1 May 26, 2016

(51) Int. Cl.
*A01H 5/02* (2006.01)

(52) U.S. Cl.
USPC ..... Plt./112

(58) Field of Classification Search
USPC ..... Plt./112
See application file for complete search history.

*Primary Examiner* — Anne Grunberg
(74) *Attorney, Agent, or Firm* — McKee, Voorhees & Sease, PLC

(57) ABSTRACT

A new variety of Climbing Miniature rose suitable for garden decoration, having flowers of orange and yellow bicolor coloration.

1 Drawing Sheet

Classification: The present invention relates to a new *Rosa hybrida* plant.

Variety denomination: The new plant has the varietal denomination 'WEKwoagorol'.

BACKGROUND OF THE INVENTION

This invention relates to a new and distinct variety of Climbing Miniature Rose. It has a non-disseminated seedling of my creation as its seed parent with the following genetic origin (Work of Art×Goldmarie) and as its pollen parent the variety known as 'WEKtorroc' (not patented).

SUMMARY OF THE INVENTION

Among the features which distinguish the new variety from other presently available and commercial rose cultivars known to the inventor are the following combinations of characteristics: its excellent color stability throughout the life of the flower, its unusual orange and yellow bicolor flower coloration and its many hairs on the peduncle and flower receptacle. The plant has a spreading climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKwoagorol' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, a non-disseminated seedling of my creation by the following combination of characteristics: whereas 'WEKwoagorol' bears medium sized flowers (about 4.8 to about 7.3 cm. in diameter) of orange and yellow bicolor coloration, the non-disseminated seedling bears significantly smaller flowers (about 3.6 to about 4.2 cm. in diameter) of yellow with light pink blush coloration. The new variety bears double flowers (about 20 to 30 petals), whereas the seed parent bears double flowers with significantly lesser petalage (about 10 to 15 petals).

The new variety may be distinguished from its pollen parent, 'WEKtorroc' by the following combination of characteristics: whereas 'WEKwoagorol' bears medium sized flowers (about 4.8 to about 7.3 cm. in diameter) of orange and yellow bicolor coloration, 'WEKtorroc' bears significantly larger flowers (about 8.5 to about 10.2 cm. in diameter) of deep pink with white stripes coloration. The new variety is classified as a climbing miniature rose with a spreading climbing growing habit with canes about 150 to about 250 cm. in length, whereas the pollen parent is classified as a climbing rose with a significantly taller and wider growing habit with canes about 305 to about 365 cm. in length.

COMPARISON WITH THE CLOSEST COMMERCIALLY AVAILABLE CULTIVAR

The new variety may be distinguished from its closest commercially available cultivar, 'MORart' (U.S. Plant Pat. No. 7,617) by the following combination of characteristics: whereas 'WEKwoagorol' bears medium sized flowers (about 4.8 to about 7.3 cm. in diameter) of orange and yellow bicolor coloration, 'MORart' bears significantly smaller flowers (about 4.0 to about 5.0 cm. in diameter) of blending orange and yellow coloration. The new variety bears double flowers (about 20 to 30 petals), whereas the closest commercially available cultivar bears flowers with heavier petalage (average about 35 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety usually bears its flowers in clusters of three to seven per stem. Flowers are borne in regular rounded to somewhat pyramidal clusters on strong medium to long stems (about 32 to about 125 cm.). Outdoors, the plant blooms abundantly and nearly continuously during the growing season. The flowers have a moderate tea to slightly fruity fragrance.

BUD

The peduncle is about 2.3 to about 3.7 cm. in length, of slender caliper (about 0.2 to about 0.3 cm. in diameter) and usually erect. It is moderately smooth, with few stipitate glands and many hairs. Peduncle color is between 146C and 146A often heavily suffused, especially on the side exposed to the sun, with between 187B and 187A.

Before the calyx breaks, the bud is about 1.0 to about 1.4 cm. in diameter at the widest point, about 1.4 to about 1.7 cm. in length, and pointed to somewhat ovoid in shape. The surface of the bud bears between 7 to 9 foliaceous appendages, few stipitate glands and some hairs, usually with slender entire foliaceous parts extending beyond the tip of the bud about ½ or more of its length. Bud color is between 137C and 137B often heavily suffused, especially on the side exposed to the sun, with between 187B and 187A.

The sepals are about 1.8 to about 2.5 cm. in length and about 0.7 to about 1.0 cm. in width at the widest point. The outer surface color of the sepal is between 137C and 137B often heavily suffused, especially on the side exposed to the sun, with between 187B and 187A. The outer surface of the sepal is smooth and bears between 0 to 4 foliaceous appendages with few stipitate glands and some hairs. The inner surface color of the sepal is near 146C broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with some stipitate glands and hairs.

The receptacle of the flower is of medium length (about 0.4 to about 0.6 cm.) and somewhat thin to average in caliper (about 0.5 to about 0.8 cm. in diameter). The receptacle is urn-shaped in form. Its surface is smooth with many hairs and very few stipitate glands with somewhat thin fleshy walls. The receptacle color is between 144A and 137B often heavily suffused, especially on the side exposed to the sun, with between 187B and 187A.

As the petals open (after the calyx breaks), the bud is about 1.2 to about 1.9 cm. in diameter at the widest point, about 1.4 to about 1.9 cm. in length, and moderately ovoid to somewhat globular in form. The color of the under surfaces of the newly opened petals is between 45B and 46B often moderately suffused with between 53A and 187B. At the point where the petal attaches, there is a large zone of between 2B and 1A. The color of the upper surfaces of the newly opened petals is between 26C and 23C sometimes moderately suffused with between 187B and 53A. At the point where the petal attaches, there is a large zone of between 3C and 4B.

BLOOM

When fully open, the bloom ranges from about 4.8 to about 7.3 cm. in diameter. Petalage is double with about 20 to 30 petals and about 5 to 17 petaloids irregularly arranged. When partially open, the bloom form is moderately globular, slightly high centered to cupped and the petals are moderately tightly spiraled to somewhat cupped with petal edges somewhat reflexed outward. When fully open, the bloom form is more cupped and the petals are loosely cupped to slightly undulated with petal edges moderately reflexed outward.

PETALS

The substance of the petals is moderately heavy and of medium thickness, with upper surfaces moderately satiny and under surfaces matte. The petals are about 1.5 to about 2.9 cm. in length and about 1.0 to about 2.9 cm. in width at the widest point. Petal margins are entire.

The outer petals are moderately obovate to somewhat rounded in shape with rounded to sometimes mucronate apices.

The inner petals are obovate to somewhat oblanceolate in shape with rounded to sometimes mucronate apices.

Petaloids are about 0.7 to about 2.4 cm. in length and about 0.3 to about 1.6 cm. in width at the widest point. Petaloids are irregularly shaped moderately oblanceolate to somewhat subulate with rounded apices.

NEWLY OPENED FLOWER

The under surface color of the outer petals is between 26D and 21D often moderately suffused with between 60A and 60B to as dark as between 187C and 46B. At the point where the petal attaches, there is a large zone of between 4C and 5D. The upper surface color of the outer petals is between 44B and 30D sometimes lightly suffused with near 60C. At the point where the petal attaches, there is a large zone of between 4B and 5C.

The under surface color of the intermediate and inner petals is between 26D and 21D sometimes lightly suffused with near 60B. The upper surface color of the intermediate and inner petals is between 33A and 30D sometimes lightly suffused with near 60D.

The under and upper surface colors of the petaloids are similar in coloration to the upper and under surfaces of the intermediate and inner petals.

The general tonality of the newly opened flower is between 33A and 30D.

THREE-DAY-OLD FLOWER

The under surface color of the outer petals is between 26D and 21D often heavily suffused with between 60B and 60C to as dark as between 60A and 46B. At the point where the petal attaches, there is a large zone of between 4C and 5D. The upper surface color of the outer petals is between 44B and 30D sometimes lightly suffused with between 60B and 45C. At the point where the petal attaches, there is a large zone of between 4B and 5C.

The under surface color of the intermediate and inner petals is between 26D and 21D often moderately suffused with between 60C and 60D. The upper surface color of the intermediate and inner petals is between 43B and 30D sometimes lightly suffused with between 60C and 45C.

The under and upper surface colors of the petaloids are similar in coloration to the upper and under surfaces of the intermediate and inner petals.

The general tonality of the three-day-old flower is between 43B and 30D.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids. The filaments are of somewhat short to medium length (about 0.3 to about 0.6 cm.) most with anthers. Filaments are between 14B and 13B in color. The anthers are small for the class and all open approximately at the same time. Anther color when immature is near 20A on the external part and near 13D on the internal part. Anther color at maturity is near 164B on the external part and near 200A on the internal part: Pollen is somewhat abundant and between 18B and 19C in color.

FEMALE REPRODUCTIVE ORGANS

Pistils vary in number (average about 120). The styles are moderately even, somewhat short to average in length (about 0.3 to about 0.6 cm.), moderately thin in caliper, and loosely bunched to somewhat separated. Stigma color is between 11A and 10A. Style color is between 145C and 150C often heavily suffused with between 53A and 53B. Ovaries are usually all enclosed in the calyx.

Hips have not been observed on this variety when grown in Wasco, Calif.

FOLIAGE

The compound leaves are usually comprised of three to seven leaflets and are borne abundantly. The five-leaflet leaves are about 6.9 to about 9.7 cm. in length and about 5.3 to about 7.1 cm. in width at the widest point, moderately leathery to somewhat crisp in texture, and glossy in finish on the upper side and somewhat glossy in finish on the under side. The leaves have a pinnate venation pattern. The terminal leaflets are about 2.8 to about 4.0 cm. in length and about 1.9 to about 2.6 cm. in width at the widest point, shaped moderately ovate to somewhat oval with acuminate apices and rounded to somewhat acute bases. Their margins are usually simply serrate.

The upper surface color of the mature leaf is between 139A and 137B. The under surface color of the mature leaf is between 137B and 137C. The under and upper colors of the leaf veins on the mature leaf are similar in coloration to the upper and under surfaces colors of the mature leaf. The upper surface color of the young leaf is between 139A and 137C, often moderately suffused with between 187A and 183A. The under surface color of the young leaf is between 146B and 137C, often moderately suffused with between 187B and 183B. The under and upper colors of the leaf veins on the young leaf are similar in coloration to the upper and under surfaces colors of the young leaf.

The rachis is light in caliper and rough. The upper side is deeply grooved with few hairs and some stipitate glands on the edges of the grooves. The under side of the rachis is rough with some stipitate glands and few small prickles. The rachis color is near 146D on the under side and near 137B on the upper side, often heavily suffused on the young leaves with between 187A and 187B.

The stipules are about 1.2 to about 1.6 cm. in length and of medium width (about 0.3 to about 0.5 cm.) with long straight points that usually turn out at an angle of more than 45 degrees and sometimes recurve toward the stem. The under and upper surface color of the stipule is between 137A and 137B often heavily suffused on the young leaves with between 187A and 187B.

The petiole is light in caliper and rough. The upper side is deeply grooved with few hairs and some stipitate glands on the edges of the grooves. The under side of the petiole is rough with some stipitate glands and few small prickles. The petiole is about 0.7 to about 1.6 cm. in length and about 0.1 to about 0.15 cm in width at the widest point. The petiole color is near 146D on the under side and near 137B on the upper side, often heavily suffused on the young leaves with between 187A and 187B.

The plant displays an above average degree of resistance to powdery mildew and rust as compared to other commercial varieties grown under comparable conditions in Wasco, Calif. The plant's winter hardiness and drought/heat tolerance are yet to be determined.

GROWTH

The plant has a spreading climbing growing habit with canes about 150 to about 250 cm. in length with full branching. It displays vigorous growth and the canes are of moderately heavy caliper for the class (about 2.4 to about 4.0 cm. in diameter at the widest point).

The color of the major stems is between 146B and 146C. They bear some large prickles that are about 0.7 to about 0.9 cm. in length. The large prickles are angled moderately downward with a short somewhat broad oval base; prickle color is between 165B and 164A often moderately suffused with between 201B and 201C. The major stem bears many small prickles of similar shape and coloration.

The color of the branches is between 146A and 137B. They bear some large prickles which are of similar size and shape to the large prickles on the major stems; prickle color is between 160B and 161B sometimes lightly suffused with near 187D. The branches bear some small prickles of similar shape and coloration.

The color of the new shoots is between 146A and 137B often heavily suffused with between 187A and 187B. They bear some large prickles which are of similar size and shape to the large prickles on the major stems; prickle color is between 160A and 152D often heavily suffused with between 187A and 187B. The shoots bear some small prickles of similar shape and coloration.

I claim:

1. A new and distinct Climbing Miniature rose plant of the variety substantially as described and illustrated herein.

* * * * *

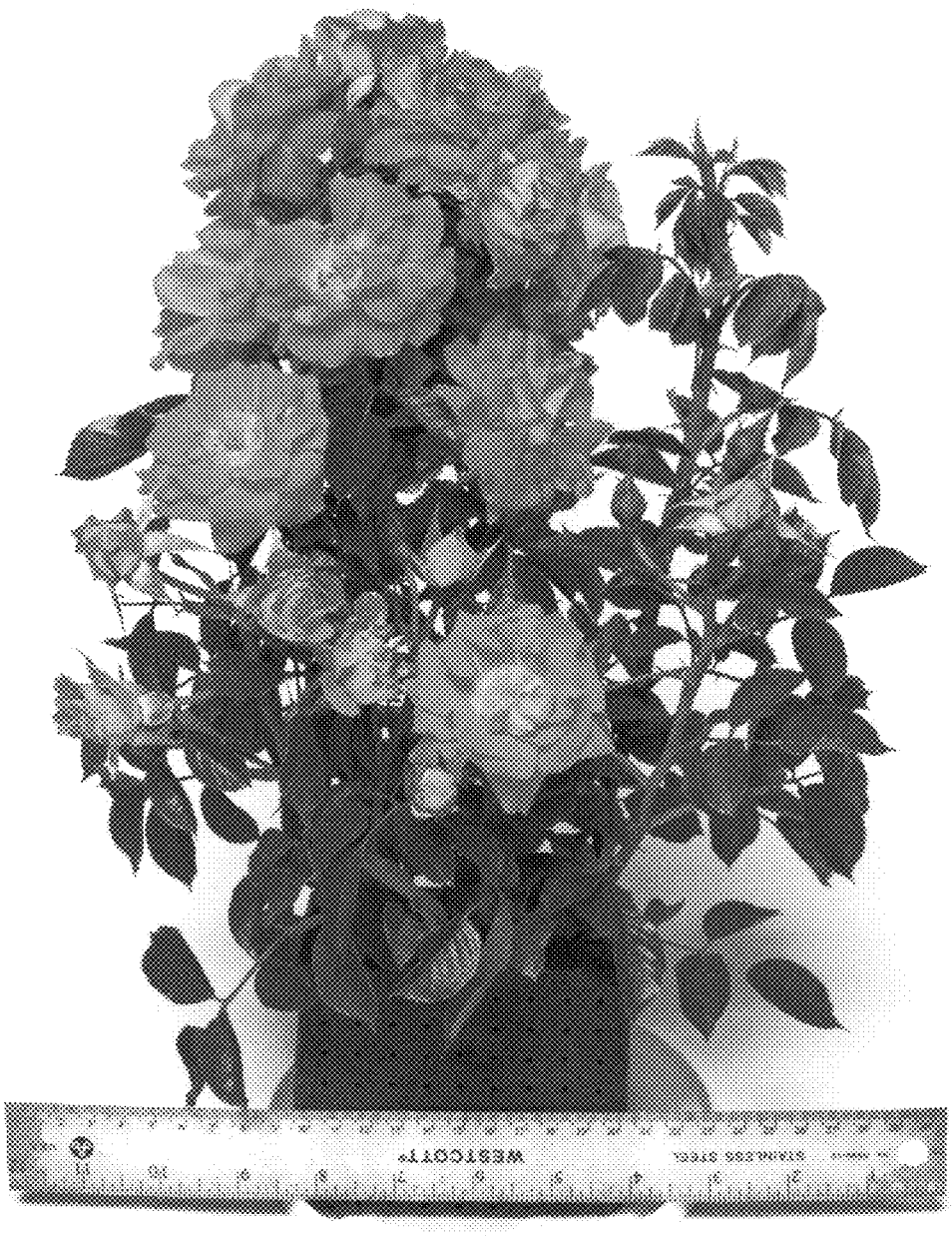
WESTCOTT
STAINLESS STEEL